United States Patent
Robinson et al.

(10) Patent No.: US 6,419,633 B1
(45) Date of Patent: Jul. 16, 2002

(54) 2D ULTRASONIC TRANSDUCER ARRAY FOR TWO DIMENSIONAL AND THREE DIMENSIONAL IMAGING

(75) Inventors: Andrew L. Robinson; Brent Stephen Robinson, both of Kirkland; Paul Detmer, Seattle, all of WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 39 days.

(21) Appl. No.: 09/663,557

(22) Filed: Sep. 15, 2000

(51) Int. Cl.[7] ................................................ A61B 8/00
(52) U.S. Cl. ........................ 600/443; 600/447; 600/460
(58) Field of Search ................................ 600/443, 447, 600/444, 459, 460; 73/628

(56) References Cited

U.S. PATENT DOCUMENTS

| | | | |
|---|---|---|---|
| 4,671,293 A | * | 6/1987 | Shaulov ........................ 600/437 |
| 5,537,367 A | | 7/1996 | Lockwood et al. |
| 5,546,807 A | * | 8/1996 | Oxaal et al. ................... 73/606 |
| 5,744,898 A | * | 4/1998 | Smith et al. ................. 310/334 |
| 5,808,962 A | | 9/1998 | Steinberg et al. |
| 5,894,646 A | | 4/1999 | Hanafy et al. |
| 5,902,241 A | | 5/1999 | Seyed-Bolorforosh et al. |
| 5,938,612 A | | 8/1999 | Kline-Schoder et al. |
| 6,014,897 A | | 1/2000 | Mo |
| 6,279,399 B1 | * | 8/2001 | Holm ........................... 73/626 |

OTHER PUBLICATIONS

Davidsen et al., "A Two–Dimensional Array for B–mode and Volumetric Imaging with Multiplexed Electrostrictive Elements," Ultrasonic Imaging 19, pp. 235–250, Duke University, Durham, NC.

* cited by examiner

Primary Examiner—Francis J. Jaworski
Assistant Examiner—Maulin M Patel
(74) Attorney, Agent, or Firm—W. Brinton Yorks, Jr.

(57) ABSTRACT

An ultrasonic 2D array has elements extending in two dimensions which can be individually controlled and operated to form a 2D array for scanning a volumetric region in three dimensions. Individual ones of the elements can also be selected and operated together to form a 1D array for scanning a planar region in two dimensions. An ultrasonic probe containing the inventive array can be quickly switched between two and three dimensional imaging modes to produce both a three dimensional image and a two dimensional image in real time.

17 Claims, 11 Drawing Sheets

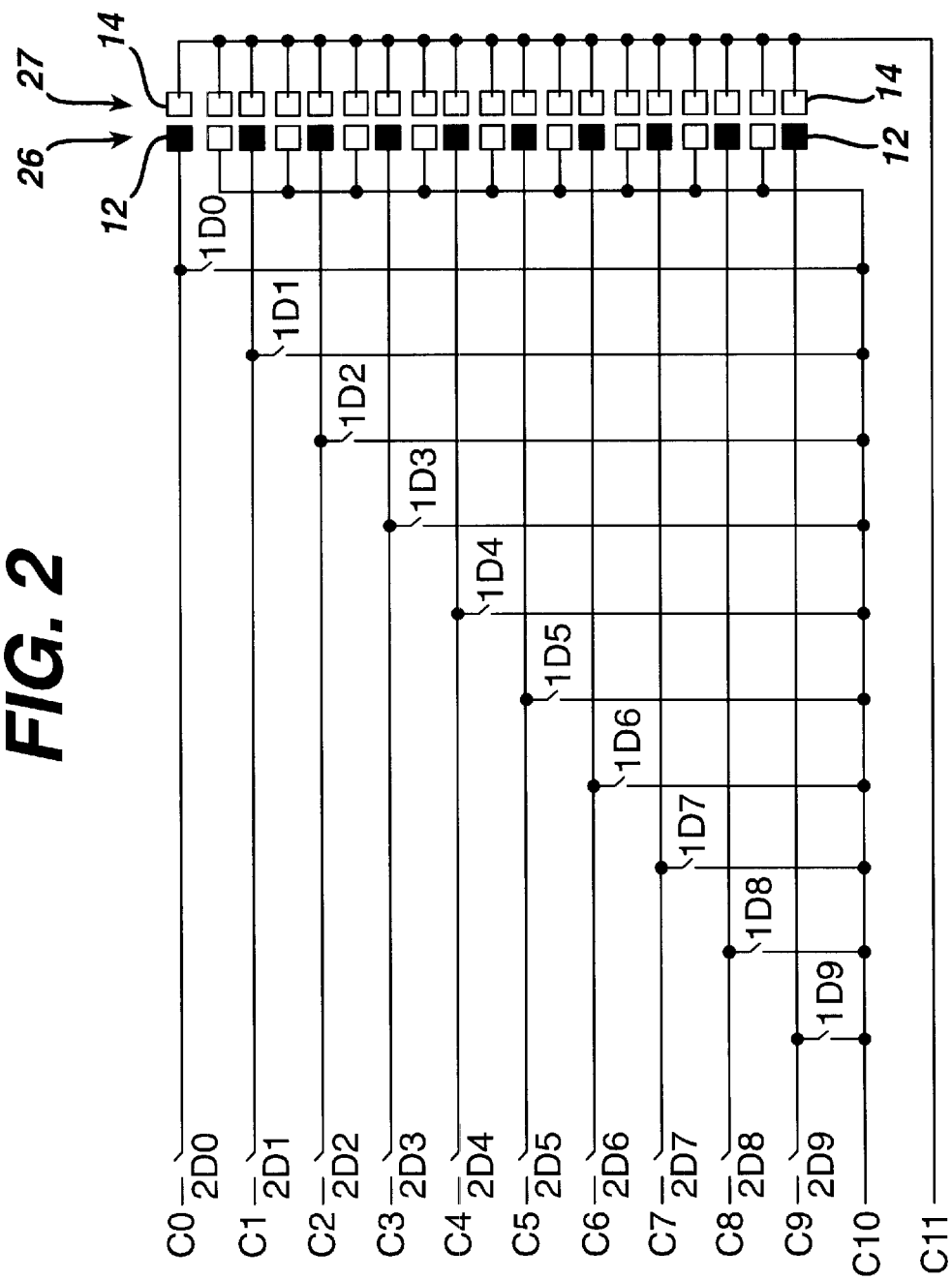

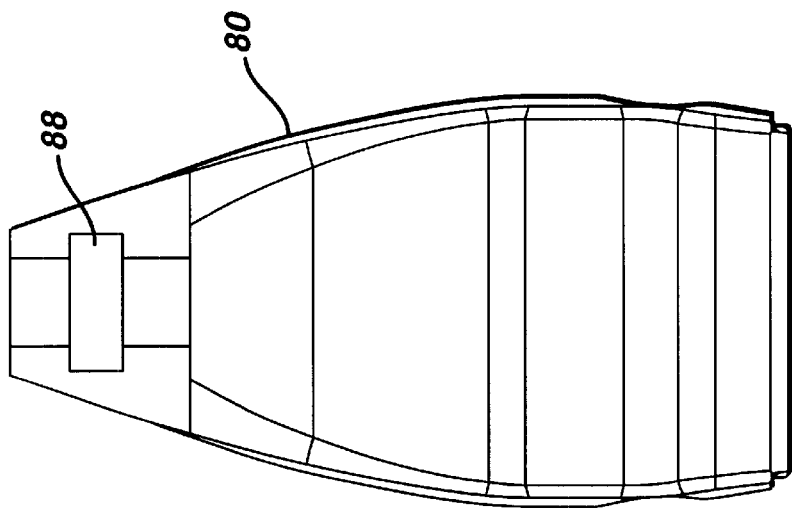
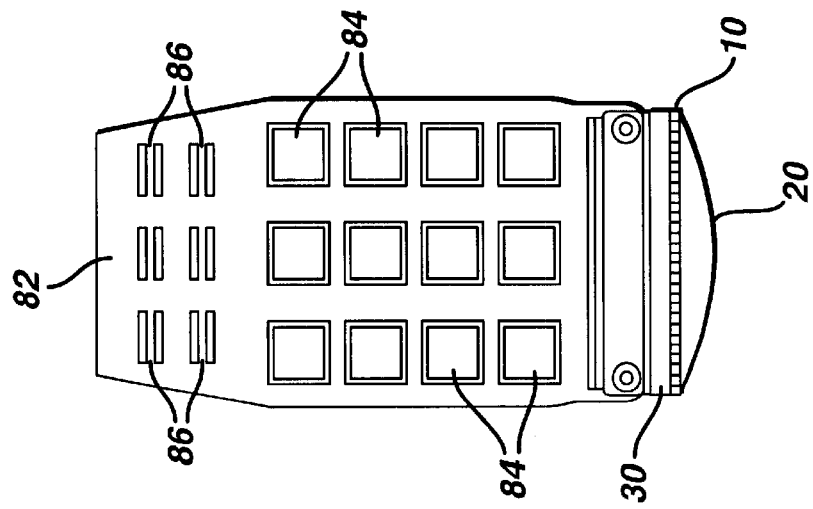

2D ULTRASONIC TRANSDUCER ARRAY FOR TWO DIMENSIONAL AND THREE DIMENSIONAL IMAGING

This invention relates to transducer arrays for ultrasonic diagnostic imaging systems and, in particular, to a two dimensional array which can be selectively operated for either two dimensional imaging or three dimensional imaging.

Both one dimensional (1D) and two dimensional (2D) transducer arrays are in use today for ultrasonic imaging. A 1D array consists of a flat row of transducer elements. A 1D array may be configured as a straight line of transducer elements or as a curved row of elements in the azimuth direction, which is the in-plane direction orthogonal to the beam directions which extend in the plane of the image in the range direction. The single row of elements may be controlled by selectively applying pulses at predetermined times to the individual elements to transmit a beam of ultrasonic energy which can be steered and focused in azimuth. The array can receive echoes from along the same beam direction. A single row of elements is confined to transmitting and receiving in a planar region in front of the emitting surface of the array. The 1D array has a fixed focus in the elevation dimension orthogonal to the image plane, which may be provided by an acoustical lens, curvature of the transducer, or both. This fixed elevational focus determines the thickness of the slice represented by the two dimensional image.

A 2D array is an array of transducer elements which extends in two dimensions, sometimes referred to as the azimuth and elevation directions, where the elevation direction is transverse to the azimuth direction. The 2D array is controlled in the same manner as the 1D array, by pulsing individual elements at selected times to transmit beams which can be steered and focused in both azimuth and elevation. 2D arrays can be either annular (composed of ring-shaped elements) or rectilinear (composed of rows and columns or other patterns of individual elements). Annular arrays formed of continuous rings can be focused in both azimuth and elevation but can only be directed straight ahead. Rectilinear 2D arrays can be focused and steered in both dimensions and hence can be used to steer beams through a three dimensional volumetric regions for three dimensional imaging.

Other, more restricted, variation of the 2D array are known, referred to as 1.5D and 1.75D arrays. A 1.5D array generally has fewer elements in the elevation direction than in the azimuth direction, and has pairs of elements symmetrically located on either side of a central row of elements. This enables the 1.5D array to be dynamically focused in the elevation direction, but the symmetrical operation of the elements on either side of the center row prohibits any elevational steering. A 1.75D array can be electronically steered in both azimuth and elevation, but only to a minimal extent as compared to a 2D array. Compared to 1D arrays, both 1.5D and 1.75D arrays are used to control slice thickness through dynamic elevation focusing.

Generally, 1D transducer arrays are optimized for use in two dimensional scanning while 2D transducer arrays are optimized for use in three dimensional scanning. Two dimensional slices of a three dimensional image can be displayed with lower image quality than a two dimensional image obtained from a 1D array. When a user wants to switch between two dimensional imaging and three dimensional imaging, the user must usually change transducer probes. It would be desirable to have a single transducer probe which could be used for both two dimensional and three dimensional imaging and which performs with the image quality of a 1D probe when used for two dimensional imaging.

In accordance with the principles of the present invention, a 2D transducer array is provided which can be used for three dimensional imaging and is switchable to operate as a 1D array for two dimensional imaging. Connections between elements of the 2D array are switched, preferably in the probe itself, so that echo signals are combined prior to being processed by the system beamformer. In an illustrated embodiment the 2D array can be operated with fully populated 1D apertures for two dimensional imaging or with sparsely populated 2D apertures for three dimensional imaging. A transducer probe of the present invention can advantageously be used to periodically acquire a two dimensional image frame using the fully-populated 1D aperture during the acquisition of a three dimensional volume of data by the sparse 2D aperture.

IN THE DRAWINGS

FIG. 2 illustrates a first switching configuration used to switch the array transducer of FIG. 1 between a sparse 2D array and a fully-populated 1D array;

FIGS. 8a and 8b illustrate the assembly of a transducer probe constructed in accordance with the principles of the present invention;

Figure 10A:
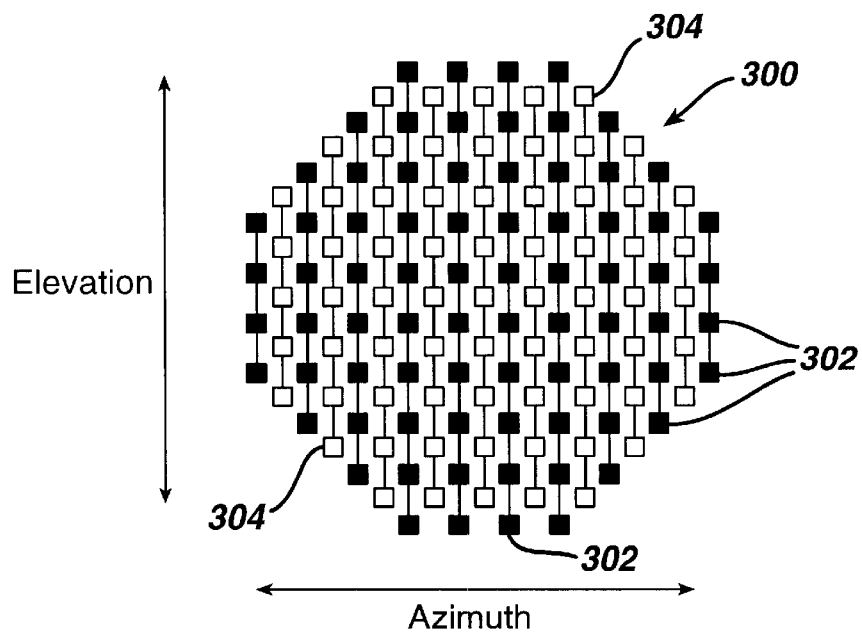
Figure 10B:
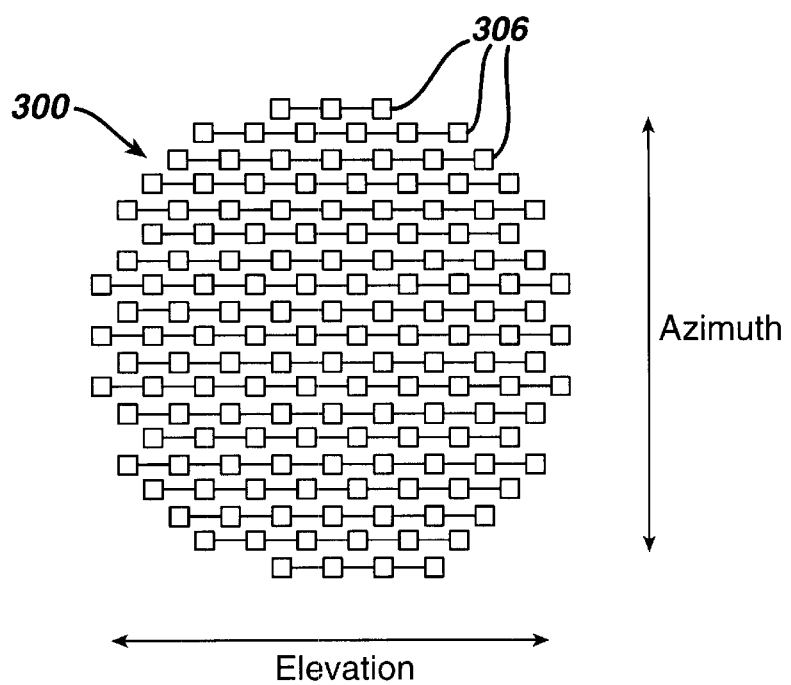
Figure 10C:
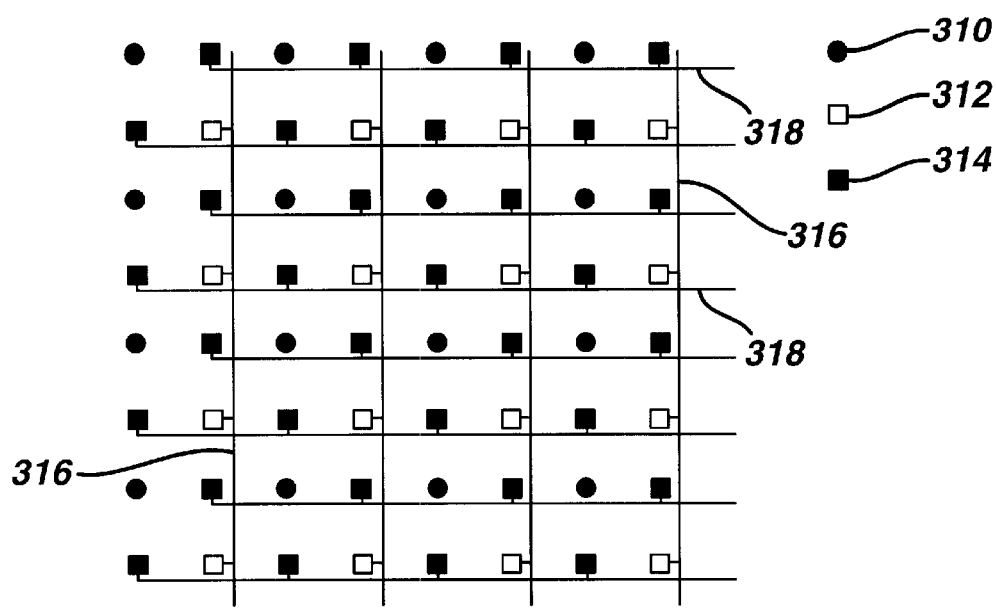
Figure 11:
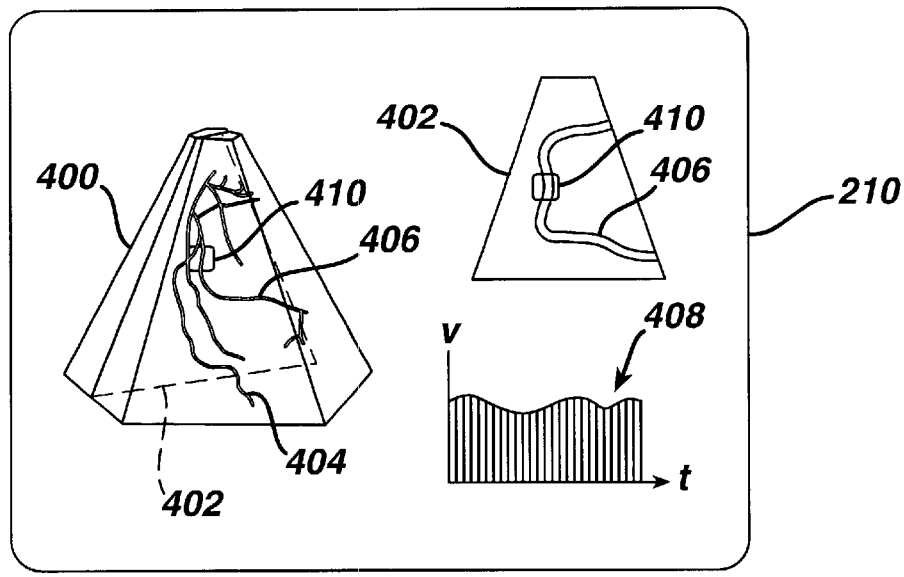
Figure 12:
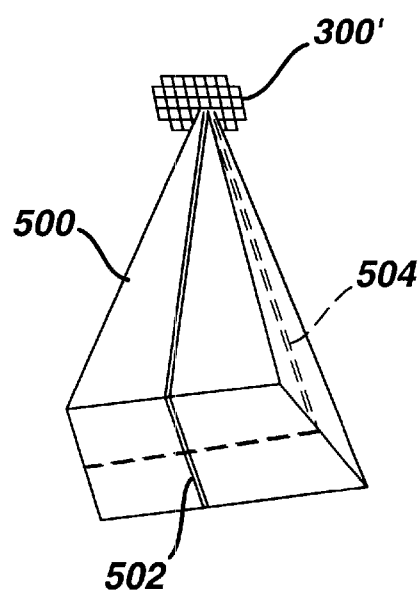

FIGS. 10a, 10b, and 10c illustrate a transducer probe of the present invention which is switchable to form two orthogonal 1D arrays;

FIG. 11 illustrates the scanning of a three dimensional volume, a planar region, and a quantified spectral display in a time interleaved manner; and FIG. 12 illustrates the scanning of a three dimensional volume and two planar regions within that volume.

Figure 1:
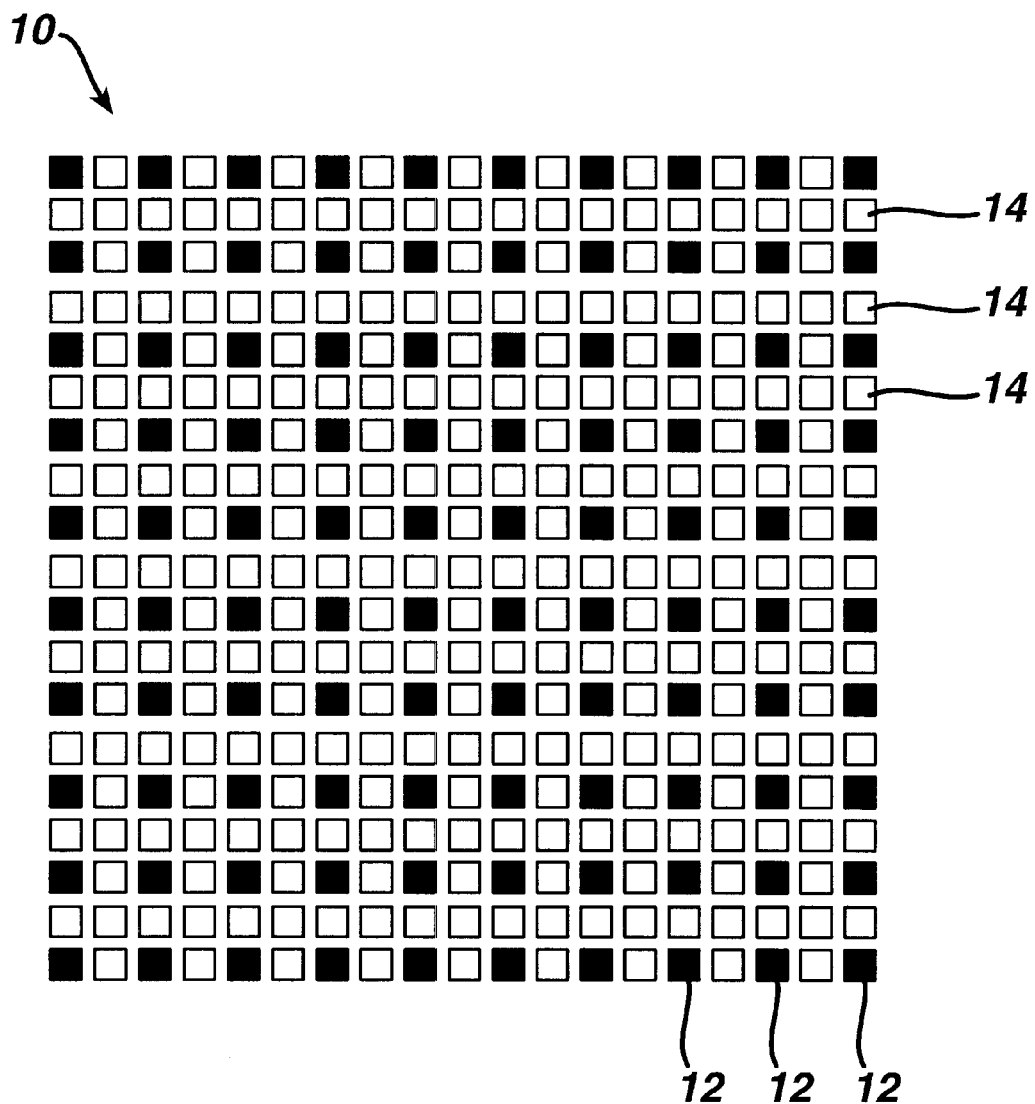
FIG. 1 is a plan view of a 2D array transducer constructed in accordance with the principles of the present invention.

Referring first to FIG. 1, a 2D array transducer constructed in accordance with the principles of the present invention is shown in a plan view. Each square in this drawing represents one transducer element in a two dimensional array of elements containing nineteen rows and nineteen columns of elements, a total of 361 elements. If this array were to be operated as a conventional 2D array, it would require 361 signal leads, one connected to each transducer element. A 19×19 array is shown for ease of illustration, however an actual constructed embodiment may be sized as a 60×60 element array or greater. Such a constructed embodiment would require 3600 signal leads. When it is considered that each signal lead is a coaxial wire, it is seen that a cable for a constructed embodiment can be inconveniently large in diameter and costly.

In the drawing of FIG. 1 alternate ones of the elements are darkly shaded. These are the elements used in this embodiment when the 2D array is to be operated as a sparse 2D array. A "sparse" array is one in which there are inactive spaces in the array aperture between the active transducer elements. In operation the active elements of the sparse 2D array 10 are individually operated to transmit and receive steered and focused ultrasound beams in the three dimensional region in front of the 2D array aperture. In this embodiment the unshaded array elements 14 are not used when the darkened elements 12 operate as a sparse 2D array. While sparse arrays have unfavorable implications for some imaging parameters such as sensitivity and grating lobes, sparse array operation can result in favorable trade-offs for other characteristics such as resolution, beamformer channel requirements, cost, frame rate, and practical cable size. The illustrated sparse 2D array has one hundred active elements 12, requiring only one hundred signal conductors in the cable, a substantial reduction from the 361 conductors required for full population of the aperture. The unused elements 14 can be left electrically open, can be connected together, can be grounded, or can be conducted to ground potential by an impedance to control the electrical boundary conditions on the elements that are not used in the sparse 2D array.

Figure 1A:
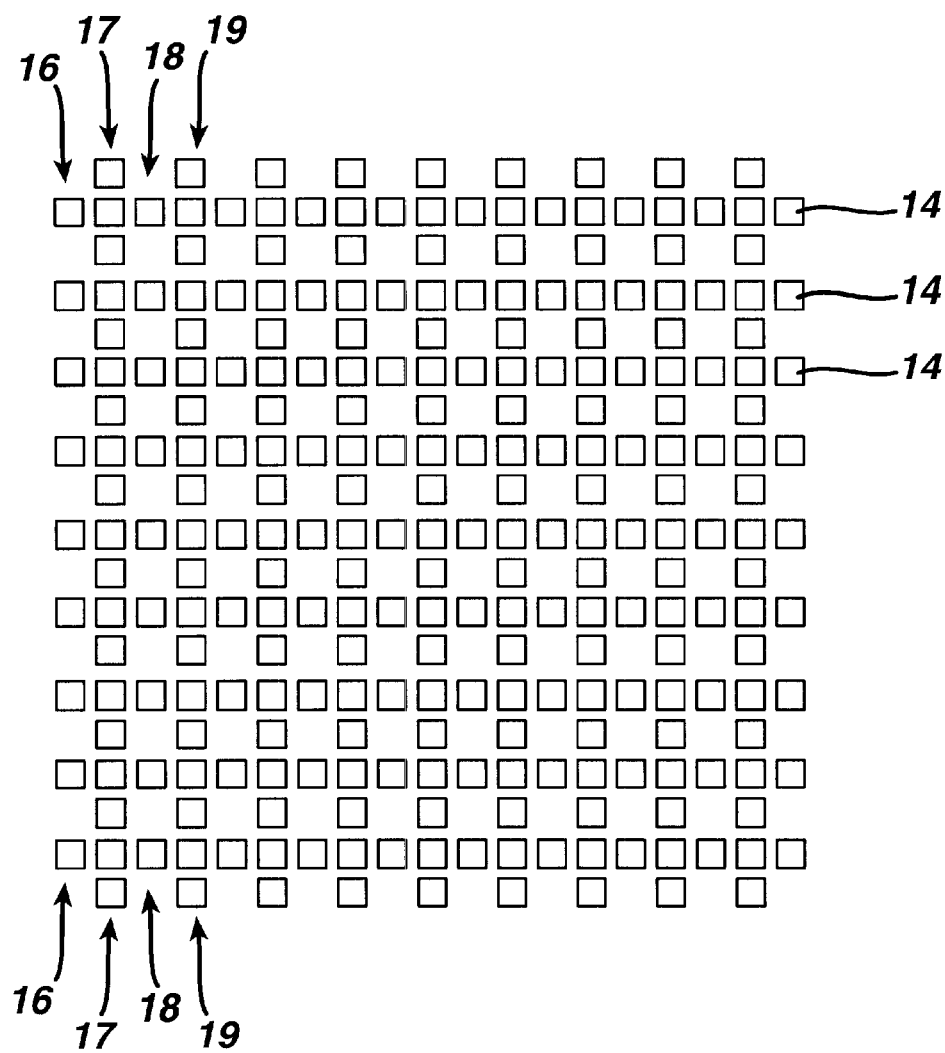
FIG. 1a illustrates the transducer elements of the embodiment of FIG. 1 which are not used when the transducer is operated as a sparse 2D array.

In an embodiment of the present invention transducer elements which are not used (not active) in the sparse 2D array aperture can be connected for use as active aperture elements when the 2D array is to be operated as a 1D array. These elements are shown in FIG. 1a for the 2D array of FIG. 1. The elements in each column 16, 17, 18, 19, etc. are connected together electrically at the acoustic stack, in the backing block/interconnect structure, or at another point in the electrical interconnect path. In the illustrated example of FIG. 1a, the 261 elements that are not used in the sparse 2D array configuration are connected to form a 1D array with 19 elements, one element per column. Only nineteen electrical connections for signal leads are needed to access the 1D array, one for each 1D element. No additional fabrication steps are required. The only additional complexity in array fabrication is to provide the means for connecting elements together in columns. Some examples of ways to do this are described below.

The resulting 1D array has holes in the locations corresponding to the elements in the sparse 2D array, and every other 1D element of the array (e.g., 16 and 18) has half as much active area as those 1D elements made up of a complete column (e.g., 17 and 19). This nonuniformity and sparseness of the 1D array can be eliminated by adding to each alternate column 16, 18, etc. the elements that comprise the sparse 2D array.

The cable required to support such an array can have three configurations. First, additional coaxes can be added to the cable, one per column, and have the beamformer in the ultrasound system sum the signals from all of the elements in each column. In this example, the cable has 119 coaxes, 100 for the active elements of the sparse 2D array (FIG. 1) and nineteen for the nineteen 1D array elements (FIG. 1a).

A second alternative, which also has 119 coaxes, uses a high-voltage multiplexer with 200 switches to include the sparse 2D array elements in their 1D array columns, so that all of the 1D elements have the same active area. Each element in the sparse 2D array requires two switches: one to connect the element to the 2D array coax, and one to connect it to the 1D coax. Such a switching configuration is shown in FIG. 2 for two array columns, column 26 which includes alternate elements 12 of the sparse 2D array aperture and column 27 which is an entire column of elements not used in the sparse 2D array configuration but used as a unitary 1D array element (e.g., columns 17 and 19 in FIG. 1a). For sparse 2D array operation, switches 2D0–2D9 connect the darkly shaded transducer elements 12 of the first column 26 to coax cables C0–C9. None of the elements 14 of the second column 27 are used in the sparse 2D array configuration; they are all connected together and go to coax cable C11 for use during 1D array operation. Those (unshaded) elements in the first column 26 which are not used in the sparse 2D array configuration are connected together, and connect directly to cable C10. In addition, the sparse 2D elements in the first column are connected to cable C10 through switches 1D0–1D9. The switch pairs 1D0/2D0 through 1D9/2D9 are operated as single-pole double-throw switches. When the 2D array is to be operated as a sparse 2D array, switches 2D0–2D9 are closed, switches 1D0–1D9 are left open and coax cables C0–C9 and the like coaxes of the other columns are used to access the shaded array elements 12. Coaxes C10, C11 and the like conductors are grounded, left floating, or connected to an impedance as desired. For 1D operation switches 2D0–2D9 are opened, switches 1D0–1D9 closed, and coaxes C10, C11 and the like conductors of the cable are used to access the elements of each array column as a single element of a 1D array.

It will be noted that the connections of coax C10 to the unshaded elements in column 26 and of coax C11 to the unshaded elements in column 27 illustrate the connections necessary to form the partially sparse 1D array configuration of FIG. 1a.

Figure 3:
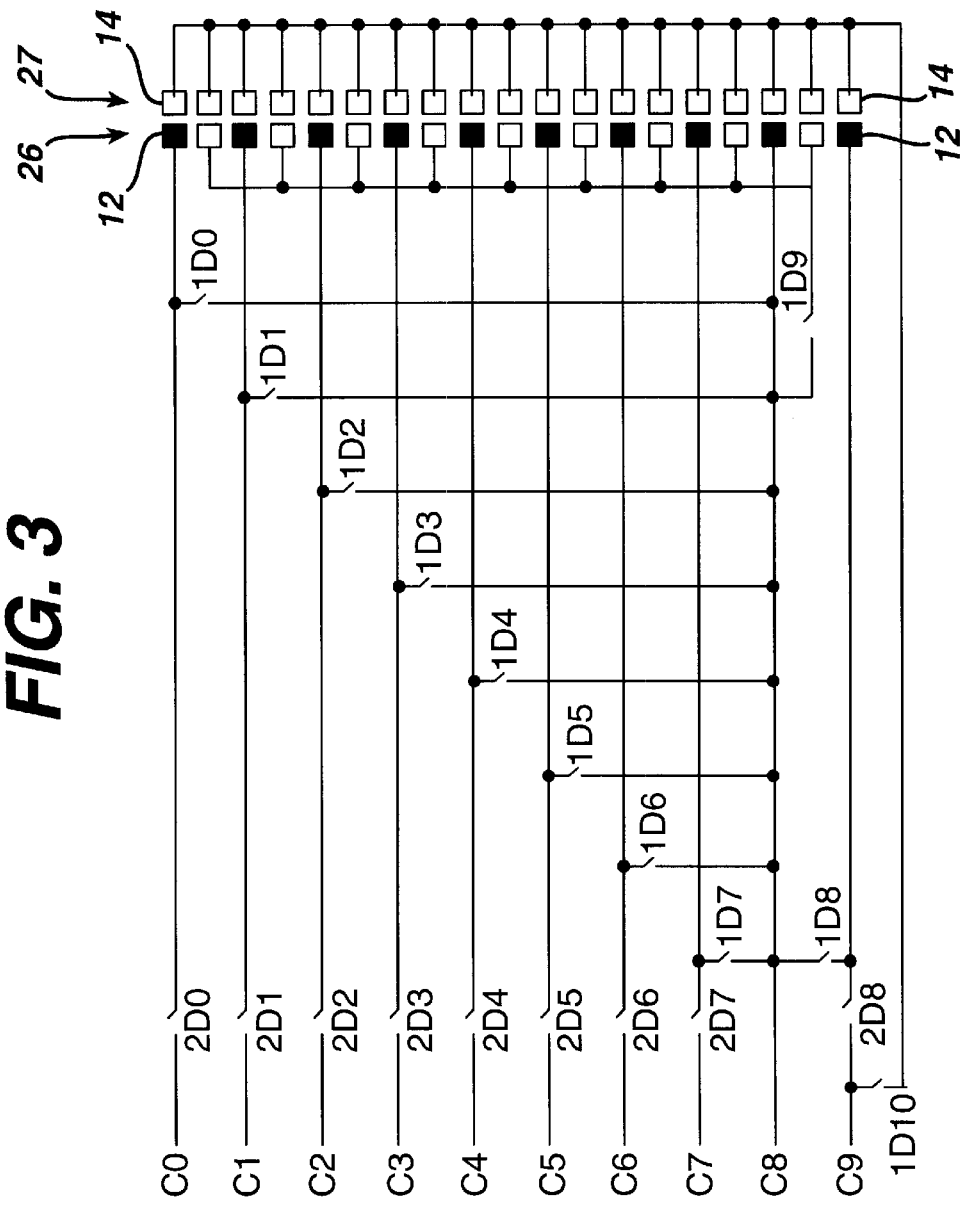
FIG. 3 illustrates a second switching configuration used to switch the array transducer of FIG. 1 between a sparse 2D array and a fully-populated 1D array.

A third implementation is to switch the 1D array onto the coaxes used by the sparse 2D array, so that no additional coaxes are needed to support the 1D array configuration. Such an arrangement is shown in FIG. 3, in which 219 switches are needed to control the array. in addition to the two switches per 2D-array element, the multiplexer requires one additional switch per column. The 2D array uses 100 coaxes when acquiring a 3D image in the sparse 2D array configuration, and 19 of those coaxes when acquiring a 2D image in the full aperture 1D configuration.

In the sparse 2D array mode, switches 2D0–2D8 are closed to connect the sparse 2D array elements 12 to coax cables C0–C9 (one element is connected directly to coax C8). In the 1D mode, switches 2D0–2D8 are open and switches 1D0–1D9 are closed to connect all of the elements of the first column 26 to coax cable C8. Switch 1D10 is also closed, connecting all of the elements of the second column 27 to coax cable C9.

Figure 4:
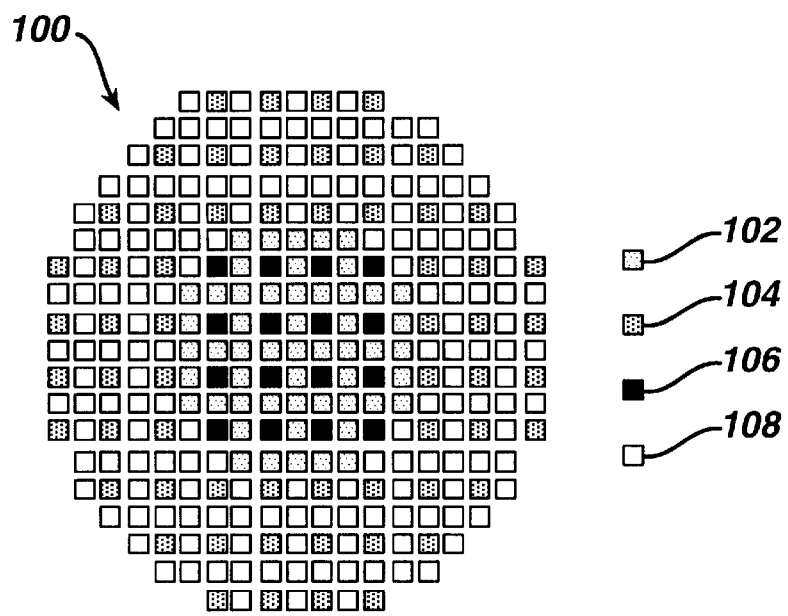
FIG. 4 illustrates a second embodiment of the present invention which utilizes different transmit and receive apertures for 3D imaging.
Figure 5:
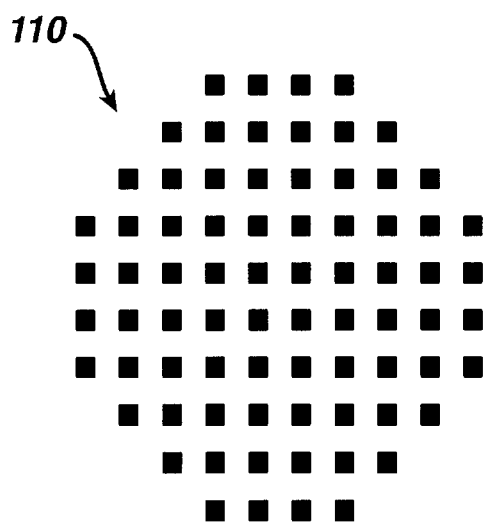
FIG. 5 illustrates the 2D sparse receive aperture of the embodiment of FIG. 4.
Figure 6:
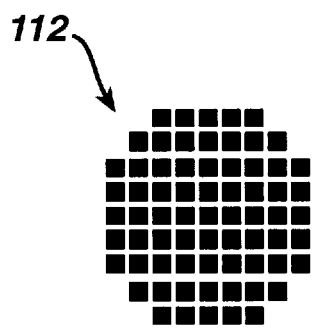
FIG. 6 illustrates a fully populated transmit aperture of the embodiment of FIG. 4.

FIGS. 4–7 illustrate another embodiment of the present invention in which different sets of elements are used for 3D imaging: a small, full 2D aperture for transmit and a large, sparse 2D aperture for receive. FIG. 4 illustrates an approximately circular subset of a 19×19 2D array 100 drawn with four types of shading as indicated to the right of the drawing. The lightly shaded elements 102 are used for transmission in the 2D array mode of operation for 3D imaging. The moderately shaded elements 104 are used for reception in the 2D array (3D imaging) mode. The darkly shaded elements 106 are used for both transmission and reception in the 2D array (3D imaging) mode. The unshaded elements 108 are not used in the 2D array (three dimensional imaging) mode. All of the elements are used in the 1D array (two dimensional imaging mode) of operation. As a result, the elements which form the sparse 2D array configuration 110 of FIG. 5, which are elements 104 and 106 of FIG. 4, are used when the array receives echo signals during three dimensional imaging as a sparse 2D array. The elements 112 used to transmit beams for the sparse 2D array mode are shown in FIG. 6, which correspond to elements 102 and 106 of FIG. 4. As the drawings illustrate, beams are transmitted in three dimensions by the small, full 2D transmit aperture of FIG. 6, to generate echoes received by the sparse 2D receive aperture of FIG. 5.

Figure 7:
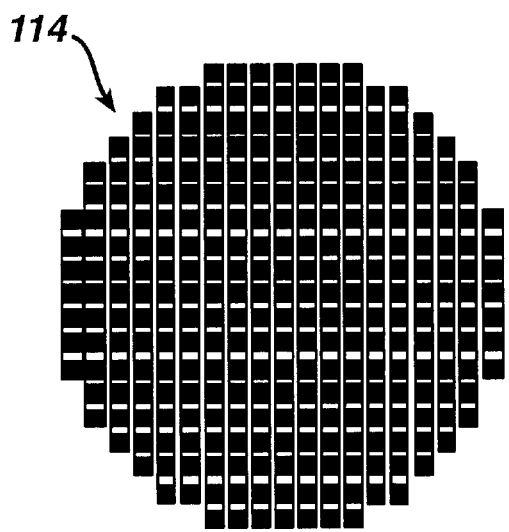
FIG. 7 illustrates the embodiment of FIG. 4 when configured as a 1D array.

In the 1D mode for two dimensional imaging, the elements of the columns are connected together as shown in FIG. 7 to form the full 1D aperture 114.

The 2D array used in FIGS. 4–7 can be a rectangular array as shown in the previous drawings, or can be configured in a shape of more than four sides such as the octagonal shape of FIG. 4. These greater sided polygonal shapes lend themselves to use of the array transducer in a rotating environment, such as the transducer for a multiplane TEE probe or rotating transthoracic probe as shown in U.S. Pat. No. 5,779,639, where they will fill a large percentage of the rotating aperture. Since the elements in the 1D array mode shown in FIG. 7 are of unequal lengths and hence exhibit unequal sensitivities, the array will usually be operated with apodization on either transmit or receive or both when used in the 1D mode.

In the embodiments of FIGS. 4–7, a multiplexer is used to switch between 2D transmit, 2D receive, and 1D modes of operation. A multiplexer substantially the same as that described in the previous embodiment may be used. The elements 108 not used in the 2D (three dimensional imaging) mode are grouped together in columns, with each column connected to a cable through a single-pole single-throw switch as described above. All of the elements 102, 104, 106 used in the 2D sparse array aperture have two switches, one to connect to a cable for 2D-array operation (transmit, receive, or both), and one to connect into a column for 1D operation. The difference between this embodiment and the prior example is that the switches cannot be operated as single-pole double-throw switches. This is because there will be situations where neither switch should be closed: during 2D-array transmit operation those 2D receive elements not in the transmit aperture would have neither switch closed; and during 2D-array receive operation those 2D transmit elements not in the receive aperture would have neither switch closed.

In all of the cases described above it may be desirable to control the electrical boundary condition on the 1D-only elements in 2D mode. This will require only one switch per column.

Referring now to FIGS. 8a and 8b, a transducer probe 120 constructed in accordance with the principles of the present invention is shown. The 2D transducer array 10 has a dome-shaped lens 20 over the transmitting/receiving side of the array to provide a greater acoustic delay in the center of the array than at the periphery of the array. This provides some of the delays required in the center of the array and reduces the longest delay demands on the beamformer. It also provides an advantageous form factor for patient contact. Behind the array is an acoustic backing block 30 which damps acoustic emissions from the back of the array. The front of the array which faces the acoustic lens 20 is covered by a metallized foil to provide a common electrical return for the elements, and signal leads are connected to the back of the array elements. Alternatively the transducer elements may be operated in the $k_{31}$ mode, in which case all electrical connections can be made from the back of the array. Flex circuit interconnections extend through the backing block 30 as described in U.S. Pat. No. 6,043,590 to provide electrical signal connections between the elements of the array 10 and components on a plurality of printed circuit boards 82. These components include multiplexer (MUX) switches 84 which are controlled to selectively interconnect elements of the 2D array to the cable assembly as described herein. Suitable MUX switch packages are the HV202 SPST FET switch packages available from Supertex, which contain both FET switches and control logic to control the switches. The control logic and FET switches of the MUX switches are connected by traces on the printed circuit board to cable connection points 86 on the printed circuit boards, which can comprise connectors. Preferably these connection points accommodate lead frames of the coaxial cables as described in U.S. Pat. No. 5,482,047.

The transducer stack and board subassembly shown in FIG. 8a, which may have one or more double-sided printed circuit boards with MUX switch packages, are enclosed in a plastic case 80, one half of which is shown in FIG. 8b. In the rear of the case 80 is an indentation which encloses the strain relief of the cable. A protective lens of soft rubber or hard plastic may be formed over the acoustic lens 20 so that the protective lens and case 80 provide an integrally sealed enclosure for the assembly shown in FIG. 8a. The embodiment of these drawings accommodates a rectilinear array transducer such as that shown in FIG. 1. Other embodiments may use an array with more than four sides, such as that shown in FIG. 4, which may be more suitable for certain cardiology applications where the probe needs to access the heart from between the ribs. Such an embodiment may be more rounded and be of a different form factor than that shown in FIGS. 8a and 8b.

Figure 9:
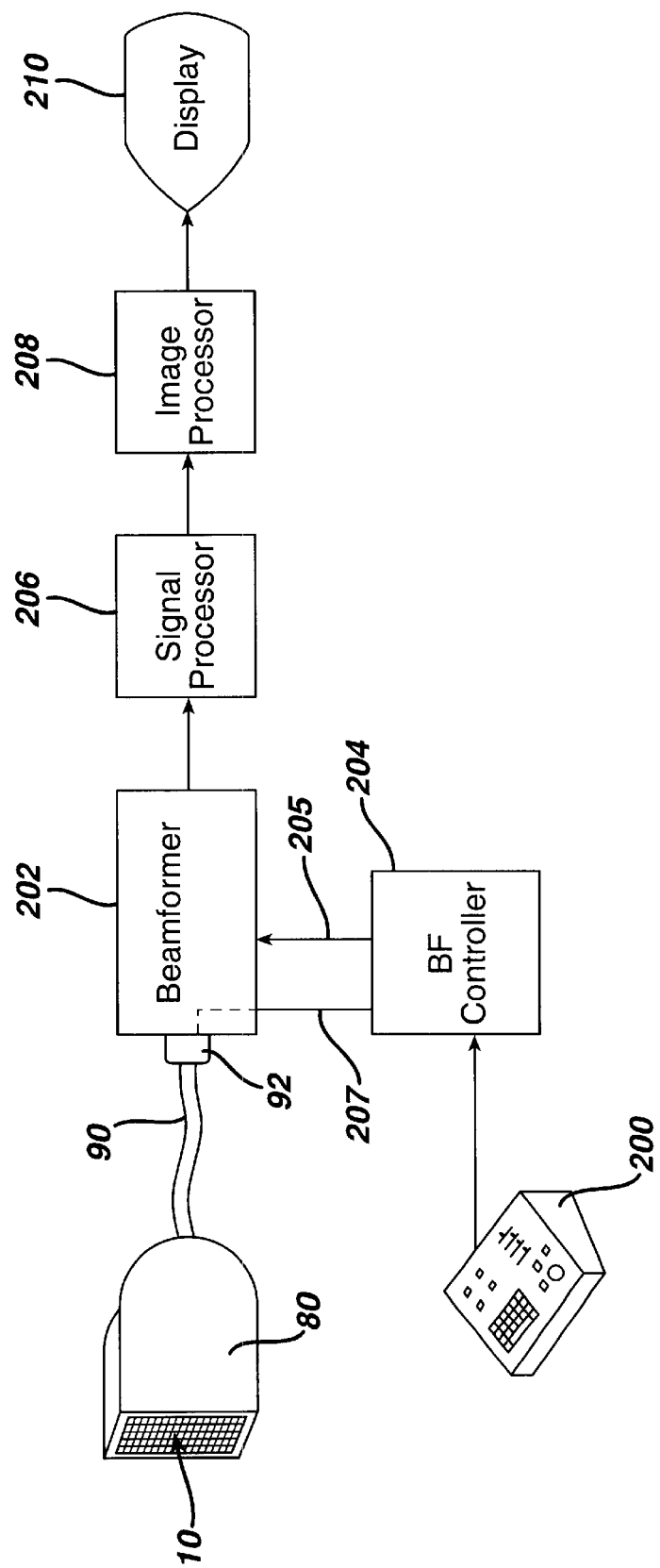
FIG. 9 illustrates in block diagram form an ultrasound system including a transducer probe of the present invention.

FIG. 9 illustrates in block diagram form an ultrasound system including a transducer probe of the present invention. The transducer probe includes a 2D array in a case 80 as described above. The transducer probe is connected to the ultrasound system beamformer 202 by a cable 90 and a probe connector 92. The beamformer 202 controls the times at which signals are applied to the elements of the 2D array which are used for transmission, and delays and combines signals received from the elements for the transmission of steered and focused beams and for the dynamic focusing and steering of received echo signals over a linear or volumetric region. Operation of the beamformer is controlled by a beamformer controller 204 which controls the timing, steering, frequency, and focusing of transmitted and received beams in the normal manner by data coupled to the beamformer 202 over a data bus 205. In addition, the beamformer controller 204 provides data over MUX control lines 207 which controls the setting of the switches that connect selected elements of the 2D array to each other and to the beamformer 202 over the cable 90. As shown in FIGS. 4–7, the 2D array can have three types of apertures: 2D transmit and 2D receive for three dimensional imaging, and 1D transmit/receive for two dimensional imaging. Thus the cable includes signal leads and MUX control signals for the switches of the 2D array 10. The beamformer controller 204 controls the beamformer in response to inputs from the user by way of the user interface 200, which may comprise a control panel or softkeys on the system display screen. For example, the user may command the system to acquire a three dimensional harmonic image using the sparse 2D array switch settings and also to periodically acquire a two dimensional Doppler flow image within the three dimensional volume using the 1D array switch settings. The beamformer controller would then control the array switches and beamformer to switch back and forth between these different modes in a time interleaved manner. The beamformed signals are B mode or Doppler processed by a signal processor 206 and formed into an image of the desired format and orientation by an image processor 208 for display on an image display 210.

The MUX switches which control the imaging mode of the 2D array can be located in several places, including within the handheld probe as shown in FIGS. 8a and 8b, within the probe connector 92, or in the beamformer 202. The beamformer usually will afford the most room for a switch printed circuit board, and will also eliminate board cooling considerations from the scanhead design. Locating the MUX switches in the probe connector 92 will enable the probe to be smaller and lighter, but at the expense of a larger cable needed to connect all of the elements of the 2D array to the connector. Locating the MUX switches in the probe itself will reduce the cable size and eliminate cable impedance effects from uncombined signals of the transducer elements.

FIGS. 10a–10c illustrate a further embodiment of the present invention by which the 2D array can be configured for imaging multiple two dimensional image planes. FIG. 10a shows a 2D array 300 in which the dark shaded elements 302 comprise the transducer elements which are operated separately as a sparse 2D array for three dimensional imaging. For two dimensional imaging the columns of elements are connected together by the MUX switches as shown by the vertical lines in the drawing to form a 1D array having elevation and azimuth dimensions indicated adjacent to the drawing. The 1D array uses both the elements 302 used for the 2D array, as well as the unshaded elements 304 which are not used for the sparse 2D array. While a full 1D array could be formed if desired, the drawing shows a sparse 1D array aperture which, as shown below, affords an ease in the switch matrix interconnection and symmetry with the sparse 1D array aperture shown in FIG. 10b. The 1D array shown in this drawing is formed by interconnecting transducer elements 306 in rows as indicated by the horizontal lines in the drawings. The elements 306 are those which are spaced between the elements 302 and 304 in the full 2D array. Thus, two 1D arrays can be formed as shown in FIGS. 10a and 10b with orthogonally oriented azimuth and elevation directions. As the drawings illustrate, both are 1D sparse arrays exhibiting the same spacing between elements and rows or columns forming the 1D array elements.

FIG. 10c illustrates how the elements of the 2D array of FIGS. 10a and 10b can be interconnected for 1D and 2D array operation. The elements represented by circles 310 are used as sparse 2D array elements for three dimensional imaging and are separately controlled; each is connected during three dimensional imaging to its own coax signal conductor of the probe cable. The elements shown as blocks 312, 314 may all be grounded, connected to ground by an impedance, or left floating during three dimensional imaging. For two dimensional imaging as a 1D array oriented as shown in FIG. 10a the columns of elements 312 are hardwired together as shown by lines 316 and each column is connected to a separate coax signal conductor of the probe cable, with each column forming a 1D array element. In addition, the elements 310 in each column are connected together to provide a 1D array element. These two sets of columns provide a ED array that is fully sampled in azimuth but is 50% sparse in elevation. For two dimensional imaging as a 1D array oriented as shown an FIG. 10b the rows of elements 314 are hardwired together as shown by lines 318 and each row is connected to a separate coax signal conductor of the probe cable, with each row forming a 1D array element.

Since a transducer array of the present invention can alternate quickly between two and three dimensional image acquisition and can provide a fuller, more sensitive 1D aperture for two dimensional imaging, it can perform spectral Doppler imaging without a change of transducer probes. FIG. 11 illustrates an imaging mode in which the probe is used to provide a two dimensional image, a three dimensional image, an a spectral Doppler display simultaneously by a time interleaved acquisition sequence. At the left of display screen is a three dimensional image 400 which is acquired by the 2D array when operating as a sparse 2D array. The three dimensional image provides an excellent survey tool by which the clinician can acquire a view of a volume of tissue and vasculature within the body. Since a volumetric region is being imaged, there is no problem with the anatomy being examined moving into and out of the image plane; the anatomy can be kept in the center of the volumetric region 400. In this case, coronary arteries 404 are imaged within the volumetric region. Additionally the orientation/location of the two dimensional image plane can be delineated in the three dimensional volume even when two dimensional imaging is not being used, as described in U.S. Pat. No. 5,353,354.

Periodically the scanning of the volumetric region in the 2D array mode is interrupted to acquire one or more scanlines of the planar image 402 in the 1D array mode. The probe is moved until the desired anatomy, in this example artery 406, is located in the plane of the image 402. The rest of the arterial branches 404 remain in the volumetric region on either side of the image plane 402. To improve the ability to see the vasculature in the image plane 402 the tissue in the volumetric region in front of the image plane, that is, between the viewer and the plane, can be made wholly or partially transparent as described in U.S. Pat. No. 5,720,291. In this example the image plane also contains a sample volume cursor 410, which can be moved in the plane by the clinician to pinpoint a location on the artery 406 at which a spectral Doppler measurement is made.

In the illustrated display mode the two dimensional image plane 402 is separately displayed on the display screen as shown at the right of the drawing, clearly showing the artery 406 of interest and the location of the sample volume 410. When the two dimensional image is separately displayed it may be desirable only to designate the location of the two dimensional image plane in the three dimensional image 400 by an outline, as described in U.S. Pat. No. 5,353,354. The two dimensional image 402 is preferably a colorflow image in which the bloodflow in the artery 406 is represented in color. For this display mode, the scanning of the volumetric region 400 would be periodically interrupted to acquire B mode lines of the two dimensional image 402 and Doppler ensembles for colorflow processing. Preferably the B mode and Doppler scanning of the planar image 402, which is done by the 2D array when switched to operated as a 1D array, is done at a higher frame rate than the frame rate of the three dimensional display. Thus, within the Lime required to scan the volumetric region once, more than one planar colorflow image is acquired and displayed as shown at the upper right side of the drawing.

The greater sensitivity of the 1D array enables a spectral Doppler display to be produced by either pulsed or continuous wave means as shown at 408 in the drawing. In this example the sample volume 401 is scanned at an even greater repetition rate than the two dimensional, image plane by operating the 2D array as a 1D array. The spectral Doppler sample volume transmit pulses, when operating in the pulsed wave Doppler mode, are time interleaved between the two dimensional imaging transmit pulses, which are in turn time interleaved between the three dimensional imaging pulses. The echo information acquired from the sample volume is Doppler processed and displayed as a spectral display as shown at 408, with the bloodflow velocity within the sample volume being shown as a function of time. Thus, a probe of the present invention can be used as a volumetric survey tool, a more sensitive two dimensional imaging probe, and a spectral Doppler probe for quantified measurements either successively or simultaneously without changing probes.

Numerous variations which take advantage of the capabilities of a probe of the present invention are also possible. For example, the display 408 in FIG. 11 can be a scrolling display of M-mode lines rather than spectral Doppler lines. In such case the sample volume 410 would be replaced by a user adjustable M-line to denote the line along which the M-mode display is to be produced. Such a display could for instance show the heart in three dimensions, a plane of the heart in two dimensions, and an M-mode display of the pulsatile motion of the heart wall along the M-line. The M-mode could be a B mode display, or could use Doppler information to produce a tissue Doppler or colorflow Doppler M-mode display. The M-lines of the M-mode display are produced at a rate which is greater than the frame rate of the two dimensional display and the three dimensional frame rate of display. The greater frame rate, resolution, and sensitivity of the two dimensional image lend themselves to contrast imaging, in particular perfusion imaging of the myocardium, as well as other types of quantified measures besides Doppler measurements. The greater sensitivity of the 1D array configuration also makes possible the imaging of a two dimensional plane with the 1D array configuration operating in the harmonic mode while the 2D array configuration is operated in the fundamental mode. Although a sparse 2D array may not exhibit sufficient sensitivity for tissue harmonic imaging when performing three dimensional scanning, this limitation is overcome by use of a fully populated 1D array for the two dimensional image, where greater sensitivity for tissue harmonic imaging is afforded.

FIG. 12 illustrates a 2D array 300' when operated to provide two planar images within a volumetric region as discussed above with reference to FIGS. 10a–10c. In this case the array is operated as a 2D array to scan a volumetric region 500. When switched to form orthogonally oriented 1D arrays, the array can scan either two dimensional plane 502 or two dimensional plane 504. A desirable format for this mode of imaging would be to display a three dimensional image of the volumetric region 500 with an adjacent planar image 502 as shown in FIG. 11 by three dimensional image 400 and planar image 402, and an additional adjacent planar image 504. As the probe is moved in relation to the body, anatomy would move into and out of the volumetric region 500, and more quickly into and out of the two image planes 502 and 504. The clinician can thus scan the body in three dimensions and in two image planes in real time. As mentioned above, the array can be operated in the fundamental mode when operated as a 2D array, and in the harmonic mode for tissue harmonic imaging of the two image planes when operated as a 1D array to take advantage of the greater sensitivity of the 1D arrays. When arrays having a grid pattern other than a square one are employed, such as the hexagonal 2D array described in U.S. Patent [application Ser. No. 09/488,583 filed Jan. 21, 2000], the image planes may be oriented on planes aligned with the grid pattern. A hexagonal 2D array may produce two or three image planes separated by 60 degrees rather than two image planes separated by 90 degrees as shown in FIG. 12.

A transducer array of the present invention can be used in all of the usual diagnostic ultrasound modes, including in different harmonic modes and with or without the use of contrast agents. The array can be used for volumetric panoramic imaging, where the array is operated as a 2D array as it is moved along the body to acquire an extended field of view image of a volumetric region. References to three dimensional imaging and volumetric scanning also include volumetric acquisition, where the data of a volumetric region is acquired but only selected planes within the volume are displayed in detail.

What is claimed is:

1. An ultrasonic diagnostic imaging scanhead comprising:
    a scanhead case having an acoustic window;
    a two dimensional array transducer having a plurality of columns and rows of transducer elements located in the case and directed for scanning through the acoustic window;
    a substrate, located in the case, and containing a plurality of single pole, single throw switches coupled to a plurality of the elements of columns of the array transducer which selectively connect the elements of the columns of the array for operation as elements of a 1D array, and selectively connect a plurality of elements of ones of the columns for individual operation as elements of a 2D array; and
    a cable coupled to the switches which connects the scanhead to an ultrasound system.

2. The ultrasonic diagnostic imaging scanhead of claim 1, wherein the substrate comprises a printed circuit board.

3. The ultrasonic diagnostic imaging scanhead of claim 1, wherein the switches act in response to signals from an ultrasound system connected by means of the cable to selectively connect elements of the two dimensional array for operation as a 2D or a 1D array.

4. The ultrasonic diagnostic imaging scanhead of claim 3, wherein the switches act to selectively connect elements of the two dimensional array for operation as a sparse 2D array or a 1D array.

5. The ultrasonic diagnostic imaging scanhead of claim 4, wherein the switches act to selectively connect elements of the two dimensional array for operation as a sparse 2D array or a full aperture 1D array.

6. The ultrasonic diagnostic imaging scanhead of claim 2, further comprising a cable connector, located on the printed circuit board, for connecting the cable to circuitry on the printed circuit board.

7. The ultrasonic diagnostic imaging scanhead of claim 1, wherein the cable includes at least one conductor for coupling switch control signals from the ultrasound system to the switches, and a plurality of signal conductors for coupling ultrasound signals from elements of the transducer array to the ultrasound system.

8. The ultrasonic diagnostic imaging scanhead of claim 1, wherein the switches act to selectively connect elements of the two dimensional array for operation as a sparse 2D receiving array or a full aperture 2D transmitting array.

9. The ultrasonic diagnostic imaging scanhead of claim 1, wherein all of the switches which selectively connect the elements of the array for 1D or 2D operation comprise single pole, single throw switches.

10. A two dimensional array of acoustically separate ultrasonic transducer elements, individual ones of which are arrayed in two dimensions and a plurality of switches, coupled to elements of the array, which selectively couple the elements for operation as a 1D array having an azimuth dimension in a first direction and an orthogonal elevation dimension, and as a 1D array having an azimuth dimension in a second direction and an orthogonal elevation dimension.

11. The two dimensional array of ultrasonic transducer elements of claim 10, wherein the 1D arrays are sparse arrays.

12. The two dimensional array of ultrasonic transducer elements of claim 11, wherein alternate elements on alternate rows of elements of the array are interconnected to operate the array as a 1D array having the azimuth dimension in the first direction, and alternate elements on alternate columns of elements of the array are interconnected to operate the array as a 1D array having the azimuth dimension in the second direction.

13. The two dimensional array of ultrasonic transducer elements of claim 10, wherein individual elements of the array are selectively operable as a 2D array.

14. The two dimensional array of ultrasonic transducer elements of claim 13, wherein individual elements of the array are selectively operable as a sparse 2D array.

15. A two dimensional array of ultrasonic transducer elements, individual ones of which are arrayed in two dimensions and selectively operable as a 2D array to scan a three dimensional volume, or as two or more 1D arrays to scan two or more image planes intersecting the three dimensional volume.

16. The two dimensional array of ultrasonic transducer elements of claim 15, wherein the two dimensional array exhibits a given grid pattern, and wherein the image planes exhibit a relative alignment which is a function of the grid pattern.

17. The two dimensional array of ultrasonic transducer elements of claim 16, wherein the grid pattern is a hexagonal grid pattern, and wherein the image planes exhibit a relative alignment of sixty degrees.

* * * * *